United States Patent [19]
Lang et al.

[11] Patent Number: 5,756,355
[45] Date of Patent: May 26, 1998

[54] LIPID MEMBRANE SENSORS

[75] Inventors: Holger Lang, Affalterbach, Germany; Bernd Koenig, Sulpice; Horst Vogel, Preverenges, both of Switzerland

[73] Assignee: Ecole Polytechnique Federale de Lausanne, Lausanne, Switzerland

[21] Appl. No.: 325,354

[22] PCT Filed: Apr. 21, 1993

[86] PCT No.: PCT/EP93/00976

§ 371 Date: Dec. 27, 1994

§ 102(e) Date: Dec. 27, 1994

[87] PCT Pub. No.: WO93/21528

PCT Pub. Date: Oct. 28, 1993

[30] Foreign Application Priority Data

Apr. 22, 1992 [EP] European Pat. Off. .............. 92303592

[51] Int. Cl.$^6$ .................. G01N 33/53; G01N 33/553; G01N 27/00; G01N 27/26

[52] U.S. Cl. .................. 435/7.21; 436/525; 436/501; 436/151; 436/806; 422/82.01; 422/82.02; 422/82.03; 204/400; 204/403; 204/416; 204/418; 204/194; 204/415; 435/287.1; 435/287.2

[58] Field of Search .................. 435/7.1, 877, 817, 435/288, 291, 287.1, 287.2; 436/525, 527, 526, 501, 287.1, 151, 287.2, 178, 806, 821, 829; 422/82.01, 82.02, 82.03; 204/400, 403, 415, 416, 418, 242, 194

[56] References Cited

U.S. PATENT DOCUMENTS 5,192,507  3/1993  Taylor et al. .................. 422/68.1

FOREIGN PATENT DOCUMENTS

| 14657/92 | 3/1992 | Australia . |
| 0 441 120 A2 | 8/1991 | European Pat. Off. . |
| WO 89/01159 | 2/1989 | WIPO . |
| WO 90/02327 | 3/1990 | WIPO . |
| WO 92/17788 | 10/1992 | WIPO . |

OTHER PUBLICATIONS

Bain et al., "Modeling Organic Surfaces with Self-Assembled Monolayers", *Angew. Chem. Int. Ed. Engl.*, 28(4), pp. 506–512 (1989).

Lang et al., "Self–Assembly of Thiolipid Molecular Layers On Gold Surfaces: Optical and Electrical Characterization", *Thin Solid Films*, 210/211, pp. 818–821 (1992).

Markowitz et al., "Self–Assembling Properties of 1,2–Diacyl–sn–glycero–3–phosphohydroxyethanol: A Headgroup–Modified Diacetylenic Phospholipid", *Langmuir*, 7(1), pp. 16–18 (1991).

Swaney, John B. Mechanism of Protein–Lipid Interaction, The Journal of Biological Chemistry, vol. 255, No. 18, pp. 8791–8797, 1980.

Williams, Brian Wesley Effect of Proteins on Fluorophore Lifetime Heterogeneity in Lipid Bilayers, vol. 29, pp. 3248–3255, 1989.

*Primary Examiner*—Christopher L. Chin
*Assistant Examiner*—Bao-Thuy L. Nguyen
*Attorney, Agent, or Firm*—Mathews, Collins, Shepherd & Gould, P.A.

[57] ABSTRACT

A bilayer lipid membrane (BLM) sensor comprising (1) a gold recording surface, (2) a first lipid layer which is an imperfect layer of a thiolipid which comprises the residue of two phospholipid molecules linked to each end of a disulphide (—S—S—) group, each through an oxyethylene (—O—CH$_2$—CH$_2$) chain which is short enough to allow the thiolipid to become anchored to the gold surface by self-assembly, but long enough to trap an aqueous layer between the gold surface and the bottom of the thiolipid layer, said thiolipid being attached to the gold surface and said imperfect layer being completed by a phospholipid which provides an unattached fluid phase at room temperature, and (3) a second lipid layer of phospholipid. The sensor is especially useful for measuring changes in electrical resistance and/or capacity when it is prepared to contain a receptor protein and an analyte containing an agonist to the receptor is contacted with the bilayer.

12 Claims, 1 Drawing Sheet

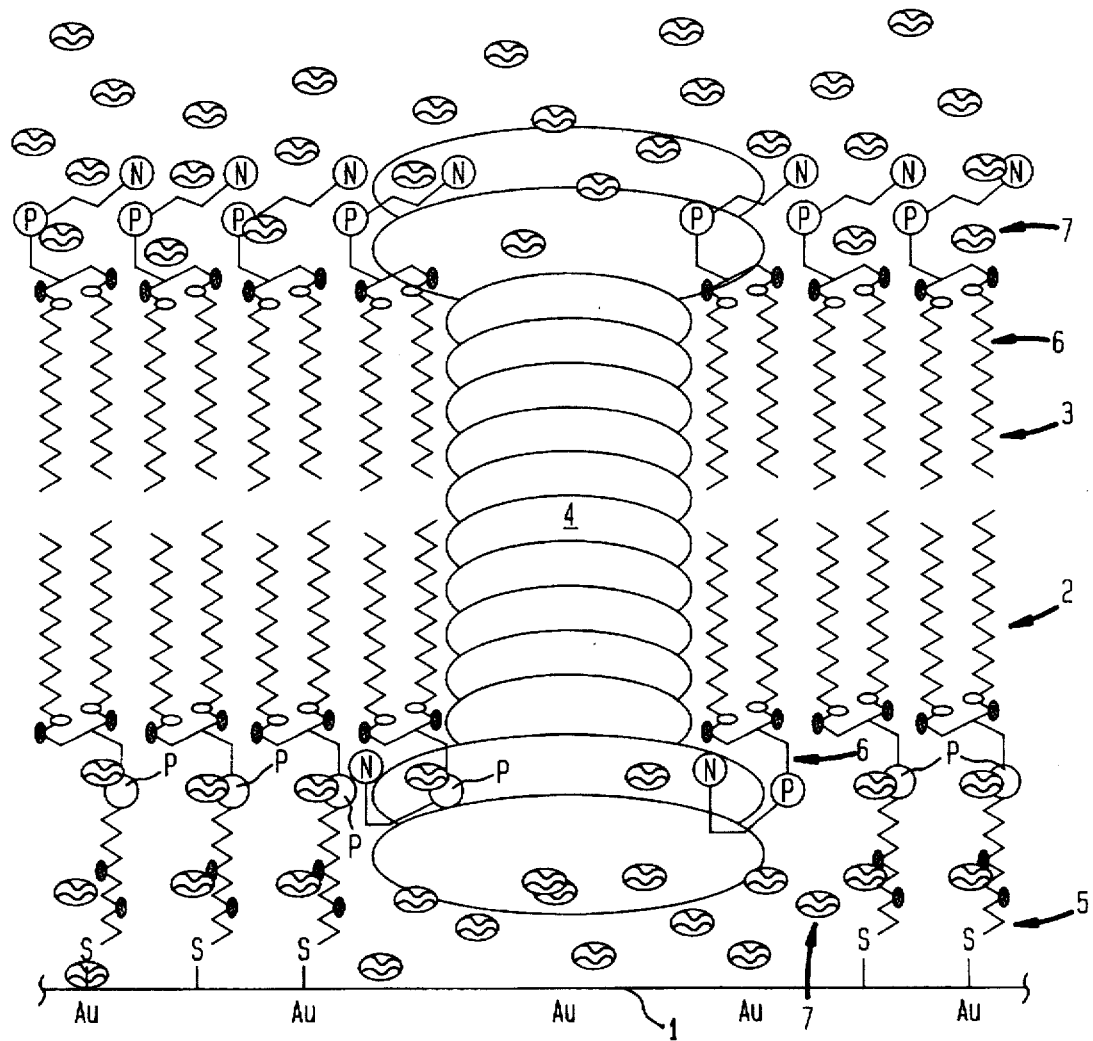

LIPID MEMBRANE SENSORS

BACKGROUND OF THE INVENTION

1. Field of the Invention

This invention relates to novel membrane sensors containing an array of self assembling lipid molecules and to the use of such sensors as biosensors.

2. Description of the Related Art

A biosensor comprises a biologically sensitive material in intimate contact with a suitable electronic device, the transducer, which converts a biochemical signal generated by the interaction between the biologically sensitive material and the surrounding fluid medium, the analyte, into quantifiable or processable electronic or optical information. A wide variety of biosensitive materials have been proposed for use in biosensors of various kinds. Enzymes, antibodies, antigens, receptor proteins, whole mammalian cells or tissues have all been suggested as being potentially useful. However in order to incorporate these materials into a sensor it is necessary to immobilise them in a way which will allow them to interact with the analyte and generate a suitable signal.

One class of biosensor is based on bilayer lipid membranes (BLMs). For a general review, see H. T. Tien et al. in "Molecular Electronics: Biosensors and Biocomputers", ed. F. T. Hong, Plenum Press, New York (1989) at pages 259–268. A sub-class of BLM biosensors mentioned therein is those which one face of the bilayer is anchored to a support while the other is in contact with a solution of analyte. The lipid bilayer is self-assembling, as the lipid molecules employed arrange themselves perpendicularly to the support in the manner:

SUPPORT: ⁻Lipid: Lipid⁻ where the symbol "⁻" denotes the negatively charged group, e.g. phosphate or acetate. The lipid bilayer contains a small number of biosensitive molecules. By way of illustration, PCT Application Publication No. WO 89/01159 (CSIRO) discloses BLMs containing a reagent providing an ion-channel, e.g. the peptide gramicidin. The FAb fragment of a divalent monoclonal antibody to human chorionic gonadotrophin (hCG) is present in the aqueous solution. The antibody blocks the ion-channel, but the block is partially released when hCG analyte is introduced into the aqueous solution, as demonstrated by a change in impedance. In these BLMs, the first layer is of dodecanethiol, the second an acetate lipid or phospholipid and support is a palladium-coated glass electrode. The thiol group provides bonding to the palladium surface. PCT Application Publication No. WO 90/02327 (Australian Membrane and Biotechnology Research Insitute) relates to detailed modifications of the earlier work. It mentions that if the lipid is directly coating a metal surface such as palladium, it would be necessary to substitute a thio residue for the phospholipid head group.

European Patent Application Publication EP-441 120 A (Yeda) points out the desirability of providing a water layer between the support and the BLM, by joining the phospholipid to the support by hydrophilic spacer arms. For example, the phospholipid with the spacer may be of formula (1):

PE—NH—(CH$_2$CH$_2$O)$_n$—CH$_2$CH$_2$SH  (1)

where PE represents a phosphatidylethanolamine residue and the number (n) of oxyethylene groups is from 7 to 25. The thiol group bonds the phospholipid to the support. This mode of attachment allows the use of mixed lipids in the composition of the lipid layers, where the minor component consists of the phospholipid with the spacer that is used for attachment to the support, while the bulk of the phospholipids define the bilayer structure (page 4 lines 34–36, FIG. 2). In other words, the bilayer is attached to a recording electrode by a few bridging, anchoring molecules, leaving a gap between the lower face of the bilayer and the upper face of the electrode, which is filled by the aqeuous medium. The BLMs are doped with "ion channels" which are normally closed, but are opened in the presence of an effector molecule. Thus the BLMs may contain an acetyl choline receptor which is alleged to give an increase in conductivity when acetyl choline is added, as analyte, to the medium surrounding the upper surface of the bilayer.

H. Lang et al. have presented a poster at the 5th International Conference on Langmuir-Blodgett Films, Paris, 26–30th August 1991 which describes BLMs in which the first layer is anchored to a gold electrode support by phospholipid molecules having a disulphide termination. They may be represented by the general formula:

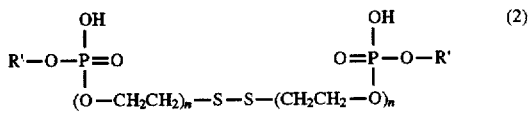

(2)

wherein R' represents the diacylglycero residue of the phospholipid DPPA (1,2-dimyristoyl-sn-glycero-3-phosphatidic acid) and n is 1, 2 or 3. The second layer of the BLM is of DMPC or POPC (1-palmitoyl-2-oleoyl-sn-glycero-3-phosphocholine). According to the poster, the thiolipid membranes, coupled to gold surfaces, show excellent long-term stability and offer an ideal matrix for incorporating membrane proteins.

SUMMARY OF THE INVENTION

It has now been found that the membranes suggested in the poster mentioned above do not function properly as sensors. The problem has been identified as excessive rigidity in the first layer and solved by introducing phospholipid (not containing any groups for binding it to the support) into the first layer, in a relatively small proportion. It will be seen, therefore, that this invention provides the very converse structure of what is suggested in the Yeda patent specification. In this invention, the first layer is a thiolipid layer in which a few phospholipid molecules are present, e.g. say 5–25 mole %, especially 5–20%. In the Yeda reference, the first layer is a phospholipid anchored by a very few thiolipid molecules. Since it has also been found desirable to use the disulfide anchoring molecules as in the poster, the invention differs from the Yeda reference in this respect also. Thiols, such as used by Yeda, do not provide such a stable anchorage.

According to the invention there is provided a BLM sensor comprising (1) a gold recording surface, (2) a first lipid layer which is an imperfect layer of a thiolipid which comprises the residue of two phospholipid molecules linked to each end of a disulphide (—S—S—) group, each through an oxyethylene (—O—CH$_2$—CH$_2$) chain which is short enough to allow the thiolipid to become anchored to the gold surface by self-assembly, but long enough to trap an aqueous layer between the gold surface and the bottom of the thiolipid layer, said thiolipid being attached to the gold surface and said imperfect layer being completed by a phospholipid which provides an unattached fluid phase at room temperature, and (3) a second lipid layer of phospholipid. Preferably the thiolipid is of formulae:

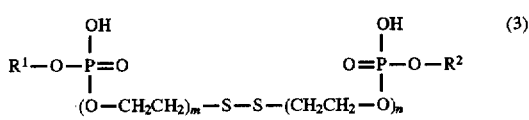

wherein m and n are from 1 to 5 and $R^1$ and $R^2$ are the residues of phospholipid molecules. Desirably m and n are the same and $R^1$ and $R^2$ are the same.

Preferably the phospholipid of the first layer comprises either a single component or a mixture of synthetic or natural phospholipids above the so-called ordered fluid-lipid phase transition temperature, to provide a fluid lipid layer.

The sensor will normally contain a ligand capable of binding with the analyte, especially a natural receptor protein capable of binding with an agonist to the receptor.

The invention includes a device comprising a sensor as defined above in the form of a cell containing an aqueous medium above the second lipid layer and means for detecting a change in a property of the lipid bilayer when an analyte (the substance to be detected or measured) which binds to the ligand is added to the cell. Preferably the aqueous medium is an electrolyte and the property in which a change is detected is electric resistance or capacitance (which can be calculated from faradaic or capacitive current, respectively).

BRIEF DESCRIPTION OF THE DRAWING

FIG. 1 illustrates schematically a BLM sensor of the invention (in pseudo-vertical section cut away centrally to show an ion channel in pseudo-perspective view).

DESCRIPTION OF TH PREFERRED EMBODIMENTS

Referring to the drawing, the BLM sensor comprises a gold surface 1, which may be an electrode, in contact with a first lipid layer indicated generally at 2, which is overlaid by a second lipid layer indicated generally at 3. A receptor protein introduced into the sensor is indicated by 4.

The thiolipid molecules 5 are shown as bonded to the gold surface by a broken disulfide bond, but this should be regarded as schematic and non-definitive: the disulfide bond may in fact be intact. In the phospholipids 6, oxygen atoms are illustrated as solid (filled) ovals, while other groups are shown by large circles as indicated. The N-atoms are those of the choline residues. Water molecules are represented by hatched ovals 7. Conveniently the phospholipids are the same in the two layers, since the layers can then be formed by simply washing out the thiolipid layer-forming components before complete reaction with the gold surface has taken place and then adding a phospholipid. The added phospholipid "completes" the imperfect first layer and forms the second layer thereover, in the same step. It can be calculated that 5–25% of the gold surface remains uncovered by the imperfect thiolipid monolayer formed in the first step. This is beneficial, because it is necessary to allow the receptor protein (or enzyme or other ligand) to penetrate the lipid bilayer fully and thereby reach the hydrophilic environment just above the gold support. This aspect is discussed below more fully.

The phospholipids can be natural or synthetic, but are conveniently selected from the phosphatidylcholine type derived from the natural lipids and mixtures thereof. These compounds are 1,2-dipalmitoyl, 1,2-dimyristoyl and 1-palmitoyl-2-oleyl-sn-glycero-3-phosphocholines, in the laevorotatory (L-) configuration, normally abbreviated to DPPC, DMPC, and POPC. DPPC has a lipid phase transition temperature of 41° C., DMPC 25° C. POPC 0° C. (These temperatures apply to lipid dispersions in water. When the lipid is present as a layer on a surface, they are a little higher). For working at normal room temperatures, of, say, 15–23° C., an approximately 1:1 molar mixture of DMPC and POPC is appropriate in the first layer to impart the desired fluidity to it. The proportions can be adjusted from this ratio to suit particular circumstances, e.g. in the range 0.5:1 to 1:1.5, preferably 0.8:1 to 1:1.2. Because of its high transition temperature, DPPC can be used only in mixtures which include POPC and then only in small proportions.

The thiolipid of formula (3) has been designed to anchor the long hydrocarbon-chain groups of the phospholipid at just the right distance from the gold support to allow formation of a hydrophilic layer of trapped water between the support and these groups, without excessive loss of rigidity of the layer. The number (n) of oxyethylene groups has been defined accordingly. The inventors have shown that a long-chain polyoxyethylene group in which n=12 does not yield a thiolipid layer. There is a failure of the self-assembly in which the thiolipid molecule binds to and orders itself with respect to the gold surface.

In formula (3) the $R^1$ and $R^2$ groups are preferably phosphatidic acid derivative residues, especially of the ester of two molecules of long-chain fatty acid with a molecule of glycerol. The long-chain fatty acid can be saturated as in palmitic or myristic or unsaturated as in oleic acid. Preferably the fatty acids have from 14–22 carbon atoms. There is no reason of principle why the disulfide should be symmetrical. That is, the $R^1$ and $R^2$ groups and values of m and n could each be the same or different, but, as a practical matter of manufacturing them, they are preferably the same.

In the preparation of the sensors, simple self-assembly takes place. The gold support is contacted with a solution or suspension, e.g. a detergent solution or aqueous vesicle suspension, of the thiolipid. The thiolipid is removed before a complete layer is formed and the phospholipid added. As explained above, conveniently this is done in a single step to complete the first layer and to form a bilayer, although there is no reason of principle why a very carefully controlled amount of a first phospholipid could not be added to complete the first layer and a less carefully controlled amount of a second phospholipid added to form the greater part (in theory, all) of the second layer.

The ligand is preferably added along with the sole or first phospholipid.

The sensor is preferably constructed in the form of a cell (small compartment) for retention of an aqueous medium above the second layer. The analyte to be detected is introduced into the aqueous medium.

The ratio of thiolipid to phospholipid in the first layer is variable by changing the time at which the phospholipid is added, typically so as to give a capacitive current of 300–1000 nA and/or a faradaic current of 100–400 nA in the first layer (before the addition of phospholipid).

The sensors of this invention find particular application when used to incorporate membrane protein receptors which can selectively bind drugs, proteins, viruses, etc., from the surrounding medium. Binding of a particular ligand to the receptor induces a structural change in the receptor which can be detected by electrical or optical means either directly or by coupling to an artificial or biological signal amplification reaction. Suitable amplification reactions include the formation of ionic channels in certain receptor proteins and the induction of enzymatic reactions which are triggered by the selective binding of the ligand to the receptor. Examples of the first type of amplification reaction are ligand- and voltage-gated ion channels such as provided by acetylcholine, GABA, glycine, 5-HT$_3$ (serotonin) receptors and sodium, potassium or calcium channel proteins. Examples of the second type of reaction are the G protein coupled receptors (adrenegic, dopaminic, muscarinic, cholerginic and serotorinergic receptors); non peptide ligands such as substance K, substance P, neuromedin, angiotensin, endothelin receptors and for peptide ligands rhodopsin and sensory receptors such as the olfactory receptors. These and other receptors are known in the art and are reviewed by A. D. Strosberg in Eur. J. Biochem 196, 1–10, (1991).

The present invention finds particular application in the formation of biosensors which incorporate membrane protein receptors which cross the lipid layer of natural membranes once or several times and thereby extend outside the lipid bilayer. These membrane proteins may be composed of a single polypeptide chain or of several sub-unit polypeptide chains. An oligomeric membrane protein complex might be composed of identical (homooligomeric) or of different (heterooligomeric) subunits. The membranes of the sensors of this invention are advantageous insofar as they bind to the surface in a manner which traps a layer of water between the solid surface and the lipid part of the first layer. Such a water layer may be several Angstroms e.g. 1 to 50 Angstroms, thick. The exact thickness of the water layer varies with the composition of the first layer. This layer enables receptor proteins which extend beyond the membrane to adopt a configuration which more closely conforms to that found in nature and enables them to respond to the binding of a ligand in a correspondingly natural fashion.

A particularly preferred sensor is one which incorporates the 5-HT$_3$ (serotonin) receptor protein. The 5-HT$_3$ receptor is known to form ligand gated ion-channels. Certain ligands specifically 5-hydroxytryptamine (serotonin) and 1-phenylbiguanide are known to act as agonists for this receptor, i.e. they induce the opening of a channel in the protein which allows ions to flow across the membrane. Certain drugs are also known which act as antagonists to this receptor, i.e. they change the structure of the protein to a closed state. These 5-HT$_3$ receptor antagonists are of pharmacological importance. The biosensors of this invention are therefore useful in the evaluation of the activity of pharmacological agents as agonists or antagonists for a biosensitive receptor protein such as 5-HT$_3$.

The sensors of this invention find use in a variety of sensing devices, especially those wherein the sensor is in intimate contact with a transducer such that changes in the electrical resistance and capacitance of the electrode upon which the bilayer is mounted can be monitored. Such biosensing devices, in the form of a cell containing an aqueous medium above the second lipid layer and means for detecting a change in a property of the bilayer when an analyte is added to the cell, form a further aspect of the invention. Other devices within the invention depend on other sensing techniques such as piezoelectric measurements or surface plasmon resonance to monitor the changes in the conformation of the biosensitive molecule, and the detection means is varied correspondingly.

The invention is illustrated by the following Examples.

EXAMPLE 1
Synthesis of bis[8-hydroxy-3,6-dioxaoctyl]disulfide 3 g (18 mmol) of 1-mercaptotriethylene glycol prepared from triethylene glycol monochlorohydrin, sodium hydrogen sulfide monohydrate and hydrochloric acid) was dissolved in 100 ml of methanol and mixed with a solution of potassium carbonate (1.3 g, 9.5 mmol in 50 ml of water). 2.3 g (9 mmol) of iodine in 100 ml of methanol was added dropwise at room temperature, thus precipitating potassium iodide. If a remaining yellow colour was observed, a small amount of sodium sulfite was added until decolouration. After evaporating to dryness, the residue was suspended in 30 ml of methylene chloride and the potassium iodide removed by filtration after cooling. The resulting solution was purified over a 5 cm silica gel column, using $CH_2Cl_2$/ MeOH (100:5) as eluant. Afterwards, it was dried under vacuum for some hours yielding 2.2 g (74%) of a nearly colourless oil.

$^1$H—NMR (CDCl$_3$): δ=2.88 (t,j=6.6 Hz,6H,—OH,—CH$_2$—S);3.55–3.58 (m,4H,—C$\underline{H}_2$—CH$_2$—OH);
3.6–3.75 [m,16H;—O—CH$_2$—CH$_2$—O—(δ=3.63,);
C$\underline{H}_2$—CH$_2$—S(δ=3.72,t,j=6.6Hz);C$\underline{H}_2$—OH].

(ii) Synthesis of bis[8-(1,2-dipalmitoyl-sn-glycero-3-phosphoryl) 3,6-dioxaoctyl]disulfide monohydrate of formula (2) wherein R represents the residue of the phospholipid DPPA (1,2-dipalmitoyl-sn-glycero-3-phosphatidic acid) and n=3

100 mg (144 µmol) of well dried 1,2-dipalmitoyl-sn-glycero-3-phosphatidic acid disodium salt (Fluka) and 78 mg (288 µmol) of 2,4,6-triisopropylbenzenesulfonyl chloride were suspended in 5 ml of anhydrous pyridine, with ultrasonication. It was warmed briefly until a clear solution was obtained and then stirred for 15 minutes. 19 mg (57 µmol) of bis(8-hydroxy-3,6-dioxaoctyl) disulfide was dissolved in 1 ml of anhydrous pyridine and added to the solution prepared above. The mixture was stirred overnight at room temperature, with exclusion of moisture. Next, 1 ml of anhydrous methylene chloride was added. The mixture was warmed briefly and stirring continued for another hour. 1 ml of water was added and, after 15 minutes, it was again warmed briefly and finally evaporated to dryness under reduced pressure. The obtained yellowish residue was suspended in 20 ml of anhydrous diethyl ether (ultrasonication) and filtered.

The filtrate was evaporated and column-purified on silica gel (30 cm×1 cm). The column was first washed with 100 ml of chloroform, the product then being eluated using a gradient of CHCl$_3$/MeOH (from 100:3) to (100:4). To eliminate traces of silica gel, the product was dissolved once more in 20 ml of diethyl ether and filtered.

Recrystallization was performed by dissolution in 1 ml of chloroform and the subsequent addition of 10 ml of acetone. After 5 hours at −15° C., the white precipitate was isolated by filtration and dried under vacuum, yielding 63 mg (69%, based on the disulfide) of a colourless solid.

|       | C     | H     | S    | P    |
|-------|-------|-------|------|------|
|       | 61.16 | 10.14 | 3.98 | 3.85 |
| found:| 61.12 | 10.03 | 3.88 | 3.75 |

$^1$H—NMR(CDCl$_3$:CD$_3$OD/2:1): δ=0.88 (t,j=6.5Hz,12H,—CH$_3$);1.27[m,96H,—CH$_2$(C$_4$-C$_{15}$)];1.61[b,8H,—CH$_2$(C$_3$)];2.28–2.36 [m,8H,—CH$_2$(C$_2$)];2.94(t,j=6.3Hz,4H,—CH$_2$—S); 3.67, (b,12H,C—O—CH$_2$—CH$_2$—O—C): 3.76 (t,j=6.3Hz,4H, S—CH$_2$—C$\underline{H}_2$—); 3.99–4.03 (m,8H, PO—CH$_2$—);4.14–4.44(m,4H,—C$\underline{H}_2$—O—CO—); 5.23 (b,2H,>CH).

$^1$H—NMR(CDCl$_3$): δ=2.97(b,8H,S—CH$_2$,P—OH,H$_2$O)
Thin layer of chromatography on silica gel:
R$_f$ 0.63 (CHCl$_3$:MeOH:H$_2$O/65.25:4)

EXAMPLES 2 AND 3

Analogously to Example 1, the corresponding compounds of formula (2) in which R is the residue of DPPC and n=1 or 2 were prepared, using bis(2-hydroxethyl)disulfide and bis(5-hydroxy-3-oxapentyl) disulfide in place of bis (8-hydroxy-3,6-dioxaoctyl)-disulfide.

Bis[2-(1,2-dipalmitoyl-sn-glycero-3-phosphoryl)ethyl] disulfide monohydrate (R=the DPPA residue, n=1) was obtained in a 57% yield after recrystallisation.

Anal. calculated for $C_{74}H_{144}O_{16}S_2P_2 \cdot xH_2O$:

|  | C | H | S | P |
| --- | --- | --- | --- | --- |
|  | 61.98 | 10.26 | 4.47 | 4.32 |
| found | 60.65 | 9.50 | 4.07 | 4.23 |

The NMR in $CDCl_3$ : $CD_3OD/2:1$ was similar to that of the n=3 compound except that the bands at 2.94 and 3.76 were shifted to 3.02 and 4.00 respectively and no separate bands at 3.67 and 3.99–4.03 were observed, the band at 4.17–4.45 being ascribed to a 12H multiplet PO—$CH_2$—CH< and —$CH_2$—O—CO—.

Bis[5-(1,2-dipalmitoyl-sn-glycero-3-phosphoryl) -3-oxapentyl]disulfide monohydrate (R=the DPPA residue, n=2) was obtained in a 72% yield after recrystallisation.

Anal. calculated for $C_{78}H_{152}O_{18}S_2P_2 \cdot xH_2O$:

|  | C | H | S | P |
| --- | --- | --- | --- | --- |
|  | 61.55 | 10.20 | 4.21 | 4.07 |
| found | 60.18 | 9.44 | 4.07 | 4.05 |

The NMR in $CDCl_3$ : $CD_3OD/2:1$ was similar to that of the n=3 compound except that the band at 3.67 was replaced by one at 3.68 ascribed to 4H, PO—$CH_2$—$CH_2$.

EXAMPLE 4

Isolation of the Agonist/Antagonist Binding Unit of the 5-$HT_3$ Receptor From Calf Brain Calf entorhinal cortex and hippocampus were isolated from freshly-dissected calf brains within two hours. All procedures were performed at 4° C. unless otherwise stated. First, the tissue from three brains (approximately 50 g) was cut into small pieces, minced for one minute in 400 ml of complex buffer solution "A" containing 20 mM HEPES, 130 mM KCl, 0.5 mM $MgCl_2$, 1 mM $CaCl_2$, 0.5 mM EDTA, 1 mM DTT, 0.1 mM PMSF, pH 7.4 and homogenized in a glass-PTFE-homogenizer. Then, the homogenate was centrifuged at 50000 g for 10 minutes to separate the membrane fraction from the soluble compounds of the cell. The supernatant was discarded and the pellet again dissolved in the 10-fold volume of buffer. It was once more homogenized and centrifuged as described above. The resulting pellet was dissolved in a small amount of complex buffer A containing 8% sucrose and stored at −50° C. until further use.

The thawed membranes were centrifuged (50000 g) for 20 minutes to isolate them from the solution containing the sucrose. To lyse still-intact cells, the pellet was suspended in a 5-fold volume of 50 mM HEPES, pH 7.4, ultrasonicated and stirred for 30 minutes. After centrifugation of the suspension (50000 g, 4° C., 20 min.), the resulting pellet was solubilized in approximately 50 ml of solution, a solution of 40 mM, with stirring. After about 1 hour, the almost-clear solution was centrifuged at 100000 g for 2 hours to pellet membrane fragments still present. The solution was then loaded at a flow rate of 10 ml/h onto a 5-hydroxytryptamine (5-HT)— agarose column (Sigma H-7136, column dimensions 2.5×0.9 cm) which had been equilibrated with the OPG/complex buffer solution. The column was washed with a 5-fold column volume of the same solution (at a flow rate of 4 ml/h) to eliminate lipids and unbound proteins. Finally, the bound 5-$HT_3$ receptor was eluted, using approximately 15 ml of 100 mM 5-HT in the OPG/complex buffer solution. To remove the excess of 5-HT and to reduce the sample volume, the solution was concentrated by ultrafiltration (Amicon cell 3, YM 10 membrane) to a final protein concentration of approximately 1 mg/ml and stored at −50° C.

(b) Activity of the Isolated 5-$HT_3$ Receptor to Bind Agonists (serotonin) and Antagonists (ICS 205-930)

The activity of the 5-$HT_3$ receptor to bind tritium-labeled ICS 205-930 was determined as follows. 1 μl samples of the receptor solution, containing 1 μg receptor protein, were mixed with different amounts of a 44.5 nM aqueous solution of the radio-labeled ICS 205-930 (6.12 μCi/ml, Sandoz AG, Basel) and made up to 500 μl with the complex buffer. After an incubation of 1.5 hours, 100 μl of polyethylene glycol 400 was added in order to precipitate the receptor. After centrifugation (10 min., 7000 g), the supernatant was separated from the pellet. The samples were mixed with 4 ml liquid scintillation cocktail (SIGNA-FLUOR - Trade Mark) and the radioactivity measured using a liquid scintillation counter (Beckman Instruments).

The isolated protein shows binding activity to agonists and antagonists of the 5-$HT_3$ receptor.

EXAMPLE 5

Preparation of a Bilayer Lipid Membrane Sensor Not in Accordance With the Invention. For Comparative Purposes (i) Formation of a First Layer, of Pure Thiolipid, on a Surface Thiolipids, dissolved in an aqueous detergent solution such as octylglucopyranoside, can spontaneously adsorb to bare gold surfaces, assembling to a single lipid bilayer supported by covalent bonds to the gold surface. The formation of this lipid layer was observed by measuring the concomitant changes of the electrode's electrical impedance and capacitance in an electrochemical cell using a standard lock-in amplifier technique.

The working electrode of the electrochemical cell consisted of a 200 nm thick gold layer with a circular area of 1 $mm^2$ on top of a 10 nm thick chromium layer which were successively vapour-deposited on the bare silicon surface of a circular trough, photolithographically produced in the 800 nm thick silicon dioxide surface layer of a silicon wafer (conductivity 3–5 Ωcm). On the back side of the silicon wafer a 10 nm thick Cr layer and a 200 nm thick Au layer were successively vapour-deposited to afford an electrical contact to the silicon electrodes.

Bare gold surfaces were prepared immersing the whole sample for one minute in a mixture of 1 g of potassium bichromate (puriss., Fluka) in 100 ml of 98% sulfuric acid (DAB, Merck) at 100° C. Next, the sample was washed abundantly with deionized water. This procedure was performed twice before placing the electrode into the electrochemical cell.

Initially, 50 μl of an aqueous 0.1 M KCl solution was added to the cell in order to measure the electrical properties of the bare gold electrode. The currents measured by a standard lock-in amplifier technique (average values from 12 independent experiments) are:
capacitive current $I_{cap}$=3400±70 nA (±2%)
faradaic current $I_{farad}$=4520±180 nA (±4%)

Then, 0.5 ml of a solution of the thiolipid/octyl-β-D-gluco-pyranoside (OGP) (0.7 mM thiolipid and 48 mM OGP in 0.1 M KCl) was added to the 50 μl 0.1 M KCl solution in the cell. The thiolipids of Examples 1–3 were each used in this example. The adsorption of the thiolipid to the gold electrode was determined by applying an alternating voltage of ±17.5 mV between the working and the Ag/AgCl reference electrode and measuring continuously the faradaic and capacitive current with the lock-in amplifier. The capacitance of the thiolipid layers formed after 10 minutes adsorption time range was between 1 and 1.5 pF/cm$^2$. If the lipid layers are washed by pure 0.1 M KCl after 72 hours, to remove the detergent, their corresponding capacitance is 0.5, 0.6 and 0.7 µF/cm$^2$ and their electrical resistance 5–10 MΩ.

(ii) Formation of a Second Layer, of Phospholipid, on Top of the First Layer of Thiolipid Treatment of the membrane prepared in (i) above with the phospholipid DPPC, DMPC or POPC yields a bilayer membrane.

The obtained capacitance values of the mixed, gold-supported lipid bilayers (comprising a first, completed thiolipid layer, attached to the gold electrode and a second phospholipid layer on top) which are listed in Table 1, are in total agreement with those of conventional, unsupported lipid bilayers which are found to be in the range of 0.7–0.8 µF/cm ; see for example: R. Benz & B. F. Gisin. J. Membrane Biology 40 293–314 (1978). These findings demonstrate the existence of a single, supported lipid bilayer, with similar electrical properties as in the case of the conventional unsupported phospholipid membranes.

EXAMPLE 6
Preparation of a Bilayer Lipid Membrane Sensor of the Invention

A gold electrode was cleaned, inserted in the electrochemical cell, and incubated with a thiolipid/octylglucopyranoside (0.7 mM/48 mM in 0.1 M KCl) as described above (Example 5). The capacitance and impedance of the electrode was continuously observed by the lock-in amplifier. After about 2–3 minutes adsorption time, when the capacitive current reached a value of about 200 nA, the thiolipid solution was completely removed and the sample, still connected to the cell, was washed several times with detergent solution E, (55 mM OGP in 0.1 M KCl), until a stable value was obtained. These values were in the range of 300–1000 nA for the capacitive current and 100–400 nA for the faradaic current. After finishing the washing process, all but about 50 µl of the solution was removed. This made it possible to measure continuously.

Then a 1 ml of a phospholipid/octylglucopyranoside solution (4.0 mM DPPC, 4.3 mM DMPC or 3.9 mM POPC, together with 41 mM OPG in 0.1 M KCl) was placed in the cell and diluted stepwise with 0.1 M KCl. Initially, 50 µl volumes were added, then 100 µl and finally 500 µl portions. The solution was completely replaced by 0.1 M KCl after no further decrease of the current response could be observed by dilution. The whole bilayer formation (which was performed many times on different samples) took between 10 and 30 minutes. The final currents measured were:
$I_{farad}$=26.2±8.6; 21.5±8.1 and 22.7±4.2 respectively;
$I_{cap}$=131.9±2.6; 108.7±11.1 and 102.3±10.3 respectively.

The final stable mixed bilayers on the gold electrodes show capacitance values of 0.8 (±10%) µF/cm$^2$ for both the POPC and DMPC phospholipids. The resistance values are in the range of 0.5–1 MΩ per 1 mm$^2$ electrode.

The mixed lipid bilayers, consisting of a mixed monolayer of thiolipids and phospholipids on the gold electrode and a second phospholipid monolayer, show very similar capacitance and resistance values to the mixed bilayers in Table 1. However, the mixed bilayers of this latter type, with a mixed first layer are necessary for the incorporation of transmembrane protein. For instance in the case of the 5-HT$_3$ receptor, no receptor could be incorporated in the types of membranes of Example 5 and Table 1.

EXAMPLE 7
(i) Incorporation of the 5-HT$_3$ Receptor Into Planar Lipid Membranes on Gold Electrodes A 1 mm$^2$ gold electrode was cleaned and inserted into the electrochemical cell as described in Example 5. First, 100 µl of the thiolipid/OPG solution (0.7 mM/48 mM in 0.1 M KCl) was added and the adsorption process followed as described in Example 6. After approximately 2 minutes, the solution was completely replaced. The sample was washed several times with 55 mM OGP in 0.1 M KCl.

A receptor-containing solution was prepared as follows: 2 mg (2.9 µmol) of DMPC, 2 mg (2.6 µmol) of POPC (i.e. an approximately 1:1 molar ratio of DMPC: POPC) and 2 mg (41 µmol) of OPG were ultrasonicated in 1 ml of 0.1 M KCl, until the solution became clear. This solution was mixed with 15 µg of the 5-HT$_3$ receptor (1 mg/ml, in 40 mM OPG and complex buffer "A" as used in Example 4). 100 µl of the receptor-containing solution was placed in the cell. After about 2 minutes, the cell solution was diluted stepwise by the addition of small portions of 0.1 M KCl. Finally, the solution was completely replaced by 0.1 M KCl. The resulting layer was used for experiments within 5 hours at most, then being removed by washing with 55 mM OGP in 0.1 M KCl and formed again using the ice-cooled receptor solution. The bilayer lipid membrane thus formed has a receptor: lipids molar ratio of about 1: 25,000. Its electrical properties were similar to the BLM of Example 6, with a capacitance of about 0.75 µF/cm$^2$ and a resistance of 0.5–1MΩ per mm$^2$ sample.

For comparison, a corresponding lipid bilayer without the receptor protein was formed by completing the imperfect thiolipid monolayer on the gold electrode with the corresponding pure phospholipid/detergent solution.

(ii) Stimulation of the 5-HT$_3$ Receptor by 5-hydroxytryptamine

50 µl portions of 5-HT solution "B" (20 µM 5-HT in 0.1 M KCl) were added successively to the layer with the incorporated receptor (still connected to the cell containing 500 µl of 0.1 M KCl). An interval of about 50 seconds was left between additions (the capacitive and the faradaic current reaching a constant value). The data obtained from two independent experiments are given in Table 2, together with 5-HT concentrations and volumes of 5-HT solution "B" added. When the concentration of 5-HT (agonist to the receptor) is increased in the surrounding aqueous environment, a typical saturation type behaviour is observed, i.e. first there is a change of the electrical properties with increasing concentration of the agonist, and at a certain agonist concentration the capacitance and resistance of the membrane remain constant.

The same experiment was performed using a lipid layer without receptor. By applying 5-HT in the same concentration range as before, no alterations of the electrical properties of the pure lipid layer were observed.

(iii) Stimulation of the 5-HT$_3$ Receptor by 1-phenylbiguanide

The construction of the receptor-containing system was performed as described above. Again, 500 µl of 0.1 M KCl was placed in the measurement cell but for stimulation, a solution "C" of 20 µM 1-phenylbiguanide, another agonist, in 0.1 M KCl was used. The successively added volumes and the resulting 1-phenylbiguanide concentrations, as well as the obtained current responses of two experiments, are given in Table 3. The results are similar to those of Table 2.

The experimental results of Table 2 and 3 show that the 5-HT$_3$ receptor is incorporated in a gold-supported lipid bilayer, preserving the capacity of the receptor to bind its agonists. The binding activity occurs in the same agonist concentration range as observed in natural, biological cells: see for example A. V. Maricq et al., Science 254, 432–437 (1991).

The same experiment was performed using the lipid bilayer without receptor. The values obtained for different 1-phenylbiguanide concentrations are given in Table 4. They show that the response of the sensor without the receptor is much lower than in the presence of sensor-immobilised receptors.

(iv) Influence of ICS 205-930 as Antagonist on the 5-HT$_3$ Receptor

The supported lipid bilayer, containing the 5-HT$_3$ receptor, was formed as described in (ii). Firstly, 500 µl of 0.1 M KCl was placed into the cell and the stimulation performed as described in (ii) using the 5-hydroxytryptamine solution "B". Next, the system was washed with 0.1 M KCl, and the measurement cell was refilled with 500 µl of a solution of 10 nM ICS 205-930 (a gift from Sandoz AG) in 0.1 M KCl. The compound has the formula (4):

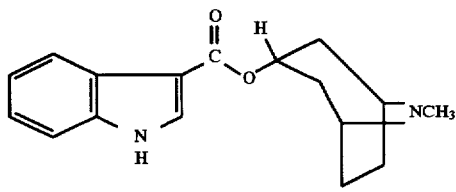

(4)

Finally, a mixture "D" of 700 µM 5-hydroxytryptamine hydrochloride and 10 nM ICS 205-930 in 0.1 M KCl was added in small portions, and keeping the ICS 205-930 concentration constant at 10 nM. After each addition, the values of the capacitive and the faradaic currents were allowed to stabilize. The data for both experiments and the successively added volumes of the different solutions are given in Table 5. Here the concentration dependence of the binding of 5-HT to the receptor was tested in the absence and in the presence of the antagonist ICS 205-930. The antagonist used has a dissociation constant to the receptor of Kd=0.7 nM. The dissociation constants of the agonists used are in the range of Kd=0.5–1 pM. The different binding properties of the agonists versus the antagonists explain the results of the experiments listed in Table 5. The 5-HT concentration necessary for binding to the receptor in the presence of 10 nM ICS 205-930 is about 40 times higher than in the absence of this antagonist. This demonstrates the ability of the receptor on the gold electrode not only to bind the agonists but also an antagonist Thus, the receptor has been reconstituted into the supported lipid bilayer in a biologically active form.

No alterations of the electrical properties of the lipid bilayer, without receptor, were observed by applying ICS 205-930.

EXAMPLE 8

Electrochemical Measurements

The working electrode was sealed onto a small hole at the bottom of the cell by means of a rubber O-ring. The O-ring was in contact with the insulating 800 nm SiO$_2$ layer and was centred around the circular electrode in order not to touch it.

A large (geometrical area about 1 cm$^2$) AgCl-coated Ag wire served as the counter/reference electrode and was fixed at a defined distance from the working electrode. The impedance measurements were made using a two-channel lock-in amplifier (EG&G model 5206) at v=120 Hz, applying U$_o$=17.5 mV RMS to the electrochemical cell. The real and imaginary parts of the impedance were obtained from the currents in phase (faradaic component I$_{farad}$) and 90° out of phase (capacitive component I$_{cap}$) with the applied voltage, respectively. These currents were measured on a 1 kΩ resistor in series with the electrodes.

The impedance and capacitance of the membrane layers on the gold electrodes were determined from the two current components, I$_{farad}$ and I$_{cap}$, using a simplified model for the electrical behaviour of the membrane with the membrane resistance R=U$_o$/I$_{farad}$ in parallel to the membrane capacitance C=I$_{cap}$/(2πvU$_o$).

TABLE 1

Capacitance in µF/cm$^2$ of bilayer membranes of pure thiolipid/phospholipid

| Phospholipid | Thiolipid of Ex. 3 (n = 2) | Thiolipid of Ex. 1 (n = 3) |
| --- | --- | --- |
| DPPC | 0.72 ± 0.05 | 0.72 ± 0.01 |
| DMPC | 0.80 ± 0.02 | 0.80 ± 0.01 |
| POPC | 0.77 ± 0.02 | 0.78 ± 0.03 |

TABLE 2

Current responses during receptor stimulation by 5-hydroxytryptamine.

| portions of B [µl] | conc. of 5-HT [µM] | Experiment 1 | | Experiment 2 | |
| --- | --- | --- | --- | --- | --- |
| | | I$_{farad}$ [nA] | I$_{cap}$ [nA] | I$_{farad}$ [nA] | I$_{cap}$ [nA] |
| — | 0 | 23.3 | 98.4 | 20.9 | 96.4 |
| 50 | 1.82 | 25 | 101.5 | 23.2 | 100 |
| 50 | 3.33 | 26.2 | 103.4 | 24.5 | 102.1 |
| 50 | 4.62 | 26.9 | 104.8 | 25.2 | 103.3 |
| 50 | 5.71 | 27.3 | 105.6 | 25.6 | 104.3 |
| 50 | 6.66 | 27.5 | 106.2 | 26.0 | 105.1 |
| 50 | 7.50 | 27.7 | 106.8 | 26.2 | 105.6 |
| 50 | 8.24 | 27.7 | 107.2 | 26.3 | 106.1 |
| 50 | 8.89 | 27.7 | 107.5 | 26.3 | 106.3 |
| 50 | 9.47 | 27.7 | 107.8 | 26.3 | 106.5 |
| 50 | 10.0 | 27.7 | 108.1 | 26.3 | 106.5 |
| 50 | 10.5 | 27.7 | 108.1 | 26.3 | 106.5 |

TABLE 3

Current responses during receptor stimulation by 1-phenylbiguanide.

| portions of C [µl] | conc. of phenylbiguanide [µM] | Experiment 1 | | Experiment 2 | |
| --- | --- | --- | --- | --- | --- |
| | | I$_{farad}$ [nA] | I$_{cap}$ [nA] | I$_{farad}$ [nA] | I$_{cap}$ [nA] |
| — | 0 | 19.7 | 94.9 | 20.3 | 96.7 |
| 50 | 1.82 | 23.6 | 96.3 | 22.7 | 97.3 |
| 50 | 3.33 | 26.1 | 97.1 | 25.0 | 98.0 |
| 50 | 4.62 | 27.7 | 97.6 | 26.6 | 98.5 |
| 50 | 5.71 | 28.9 | 98 | 28.3 | 99.2 |
| 50 | 6.67 | 29.7 | 98.3 | 29.0 | 99.4 |
| 50 | 7.50 | 30.1 | 98.4 | 29.5 | 99.5 |
| 100 | 8.89 | 30.6 | 98.5 | 29.8 | 99.6 |
| 100 | 10. | 30.8 | 98.6 | 30.0 | 99.6 |
| 200 | 11.67 | 31.1 | 98.6 | 30.3 | 99.6 |
| 200 | 12.86 | 31.2 | 98.6 | 30.4 | 99.6 |
| 500 | 14.74 | 31.2 | 98.6 | 30.4 | 99.6 |

TABLE 4

Current responses during treatment of a pure lipid layer with 1-phenylbiguanide.

| conc. of 1-phenylbiguanide [µM] | $I_{farad}$ [nA] | $I_{cap}$ [nA] |
|---|---|---|
| 0 | 21.3 | 99.5 |
| 7.5 | 20.9 | 96.5 |
| 14.74 | 20.7 | 96.4 |

TABLE 5

Current responses during receptor stimulation by 5-hydroxytryptamine, in the absence and presence of 10 nM ICS 205-930.

| portions of B [µl] | conc. of 5-HT [µM] | without ICS $I_{farad}$ [nA] | without ICS $I_{cap}$ [nA] | portions of D [µl] | conc. of 5-HT [µM] | with 10 nM ICS $I_{farad}$ [nA] | with 10 nM ICS $I_{cap}$ [nA] |
|---|---|---|---|---|---|---|---|
| 3 | 0.1 | 89.0 | 16.6 | 10 | 14 | 89.1 | 16.1 |
| 50 | 1.8 | 90.3 | 17.8 | 90 | 117 | 89.8 | 18.1 |
| 50 | 3.3 | 91.0 | 18.9 | 100 | 200 | 90.2 | 19.1 |
| 50 | 4.6 | 91.5 | 19.4 | 100 | 263 | 90.4 | 19.7 |
| 50 | 5.7 | 91.8 | 19.8 | 100 | 311 | 90.6 | 20.2 |
| 50 | 6.7 | 92.0 | 20.1 | 100 | 350 | 90.7 | 20.5 |
| 50 | 7.5 | 92.1 | 20.3 | 100 | 382 | 90.7 | 20.7 |
| 100 | 8.9 | 92.3 | 20.7 | 100 | 408 | 90.7 | 20.8 |
| 100 | 10.0 | 92.5 | 21.0 | 100 | 431 | 90.7 | 20.9 |
| 200 | 11.7 | 92.6 | 21.2 | 500 | 450 | 90.7 | 20.9 |
| pure | 20.0 | 92.6 | 21.2 | pure | 700 | 90.7 | 20.9 |

We claim:

1. A bilayer lipid membrane sensor comprising
   (1) a gold recording surface,
   (2) a first lipid layer comprising
      (a) a thiolipid having two phospholipid molecules, each linked through one or more —(—O—CH$_2$—CH$_2$)— units to each end of a disulphide (—S—S—) group, said one or more —(—O—CH$_2$—CH$_2$)— units being short enough to allow the thiolipid to become anchored to the gold surface by self-assembly through the sulfur atom of the broken or intact disulfide group, but long enough to trap an aqueous layer between the gold surface and the bottom of the thiolipid layer, said thiolipid being attached to and covering from 75 to 95% of the gold surface, and
      (b) a phospholipid providing an unattached fluid phase at room temperature and constituting the remaining 25 to 5% of the first lipid layer,
   (3) a second lipid layer of phospholipid, and
   (4) a ligand within the lipid layers capable of binding with an analyte.

2. A sensor according to claim 1, wherein the phospholipid providing the unattached fluid phase of the first lipid layer is a mixture of 1,2-dimyristoyl-sn-glycero-3-phosphocholine and 1-palmitoyl-2-oleoyl-sn-glycero-3-phosphocholine.

3. A sensor according to claim 2, wherein the ratio of 1,2-dimyristoyl-sn-glycero-3-phosphocholine and 1-palmitoyl-2-oleoyl-sn-glycero-3-phosphocholine in the mixture is from 0.5:1 to 1:1.5 molar respectively.

4. A sensor according to claim 1, wherein the phospholipid providing the unattached fluid phase of first lipid layer and the phospholipid of the second lipid layer are the same phospholipid.

5. A sensor according to claim 1 wherein a thin water layer is trapped between the gold surface and the bottom of the thiolipid layer.

6. A sensor according to claim 1 wherein the thiolipid is of the formula:

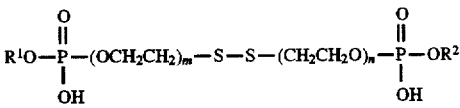

wherein each of m and n has a value of from 1 to 5 and each of $R^1$ and $R^2$ is the residue of a phospholipid molecule.

7. A sensor according to claim 5, wherein the water layer has a thickness of from 1 to 50 Angstroms.

8. A sensor according to claim 1 wherein the ligand is a natural receptor protein.

9. A sensor according to claim 8, wherein the receptor is an ion channel protein.

10. A sensor according to claim 9, wherein the receptor is the 5-HT$_3$ (serotonin) receptor.

11. A device comprising a sensor according to claim 8 in the form of a cell containing an aqueous medium above the second lipid layer and means for detecting a change in a property of the lipid bilayer when the analyte which is an agonist or antagonist for the natural receptor protein is added to the cell.

12. A device according to claim 11 wherein the aqueous medium is an electrolyte and the property is electrical resistance or capacitance.

* * * * *

UNITED STATES PATENT AND TRADEMARK OFFICE
CERTIFICATE OF CORRECTION

PATENT NO. : 5,756,355
DATED : May 26, 1998
INVENTOR(S): Holger Lang, Bernd Koenig, and Horst Vogel It is certified that error appears in the above-identified patent and that said Letters Patent is hereby corrected as shown below:

On the title page, item [75],

Bernd Koenig's address should read: "St. Sulpice"

Column 6, After line 48 and before the table

-- $C_{82}H_{160}O_{20}S_2P_2 \cdot xH_2O$ --

Signed and Sealed this

Thirtieth Day of March, 1999

Q. TODD DICKINSON

*Attest:*

*Attesting Officer*    Acting Commissioner of Patents and Trademarks